United States Patent
Gorski et al.

(10) Patent No.: US 11,778,987 B2
(45) Date of Patent: *Oct. 10, 2023

(54) UNMANNED AERIAL VEHICLE (UAV)-BASED SYSTEM FOR COLLECTING AND DISTRIBUTING ANIMAL DATA FOR MONITORING

(71) Applicant: Sports Data Labs, Inc., Royal Oak, MI (US)

(72) Inventors: Mark Gorski, Royal Oak, MI (US); Vivek Khare, Cupertino, CA (US); Stan Mimoto, Bethel Island, CA (US)

(73) Assignee: Sports Data Labs, Inc., Royal Oak, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/071,625

(22) Filed: Oct. 15, 2020

(65) Prior Publication Data

US 2021/0022321 A1 Jan. 28, 2021

Related U.S. Application Data

(63) Continuation of application No. 16/517,012, filed on Jul. 19, 2019, now Pat. No. 10,980,218.

(51) Int. Cl.
*A01K 29/00* (2006.01)
*A61B 5/00* (2006.01)
(Continued)

(52) U.S. Cl.
CPC ............ *A01K 29/00* (2013.01); *A61B 5/0002* (2013.01); *A61B 5/02055* (2013.01); *B64C 39/02* (2013.01); *A61B 3/113* (2013.01); *A61B 5/021* (2013.01); *A61B 5/02438* (2013.01); *A61B 5/0816* (2013.01); *A61B 5/1112* (2013.01); *A61B 5/1176* (2013.01);
(Continued)

(58) Field of Classification Search
None
See application file for complete search history.

(56) References Cited

U.S. PATENT DOCUMENTS 10,980,218 B2 * 4/2021 Gorski .................... A01K 29/00
2016/0266577 A1 * 9/2016 Kerzner ........... G08B 13/19697
(Continued)

OTHER PUBLICATIONS

U.S. Appl. No. 62/834,131, filed Apr. 5, 2019, Applicant: Sports Data Labs, Inc., 46 pgs.
(Continued)

*Primary Examiner* — Curtis A Kuntz
*Assistant Examiner* — Jerold B Murphy
(74) *Attorney, Agent, or Firm* — Brooks Kushman P.C.

(57) ABSTRACT

An unmanned aerial vehicle-based data collection and distribution system includes a source of animal data that can be transmitted electronically. The source of animal data includes at least one sensor. The animal data is collected from at least one target individual. The system also includes an unmanned aerial vehicle that receives the animal data from the source of animal data as a first set of received animal data and a home station that receives the first set of received animal data. Characteristically, the unmanned aerial vehicle includes a transceiver operable to receive signals from the source of animal data and to send control signals to the source of animal data.

35 Claims, 6 Drawing Sheets

(51) Int. Cl.
  *A61B 5/24* (2021.01)
  *B64C 39/02* (2023.01)
  *A61B 5/0205* (2006.01)
  *A61B 3/113* (2006.01)
  *A61B 5/021* (2006.01)
  *A61B 5/024* (2006.01)
  *A61B 5/08* (2006.01)
  *A61B 5/11* (2006.01)
  *A61B 5/1171* (2016.01)
  *A61B 5/145* (2006.01)
  *B64U 101/00* (2023.01)

(52) U.S. Cl.
  CPC ....... *A61B 5/14532* (2013.01); *A61B 5/14542* (2013.01); *A61B 5/14546* (2013.01); *A61B 5/24* (2021.01); *A61B 5/4266* (2013.01); *A61B 5/4504* (2013.01); *A61B 5/4519* (2013.01); *A61B 5/4875* (2013.01); *A61B 5/6804* (2013.01); *A61B 5/6861* (2013.01); *A61B 2503/12* (2013.01); *A61B 2503/40* (2013.01); *A61B 2560/0252* (2013.01); *A61B 2562/0204* (2013.01); *A61B 2562/029* (2013.01); *B64U 2101/00* (2023.01)

(56) References Cited

U.S. PATENT DOCUMENTS

| | | | |
|---|---|---|---|
| 2017/0193308 A1 | 7/2017 | Byuse et al. | |
| 2017/0202185 A1* | 7/2017 | Trumbull | G16H 40/67 |
| 2017/0251633 A1* | 9/2017 | Womble | A01K 15/025 |
| 2017/0330466 A1* | 11/2017 | Demetriades | G08G 5/0086 |
| 2018/0008797 A1* | 1/2018 | Kozloski | A61M 21/00 |
| 2018/0091875 A1* | 3/2018 | Bryson | A61B 5/0022 |
| 2018/0146645 A1* | 5/2018 | Arbel | G06Q 10/087 |
| 2018/0157259 A1 | 6/2018 | Myslinski | |
| 2018/0279583 A1* | 10/2018 | Yajima | A01K 11/004 |
| 2018/0314251 A1 | 11/2018 | Kamalakantha et al. | |
| 2019/0095687 A1 | 3/2019 | Shaw et al. | |
| 2019/0096232 A1 | 3/2019 | Wedig et al. | |
| 2019/0098433 A1 | 3/2019 | Shaw et al. | |

OTHER PUBLICATIONS

Int'l Search Report & Written Opinion dated Oct. 22, 2020 for PCT/US2020/042705, 13 pgs.
Office Action dated Sep. 25, 2020 for S.N. U.S. Appl. No. 16/517,012, 9 pgs.
Notice of Allowance dated Sep. 25, 2020 for U.S. Appl. No. 16/517,012 filed Jul. 19, 2019, 9 pgs.
Non-Final Office Action dated Aug. 11, 2020 for U.S. Appl. No. 16/517,012 filed Jul. 19, 2019, 26 pgs.
Non-Final Office Action dated Dec. 24, 2020 for U.S. Appl. No. 16/517,012, filed Jul. 19, 2019, 25 pgs.

* cited by examiner

UNMANNED AERIAL VEHICLE (UAV)-BASED SYSTEM FOR COLLECTING AND DISTRIBUTING ANIMAL DATA FOR MONITORING

CROSS-REFERENCE TO RELATED APPLICATIONS

This application is a continuation of U.S. application Ser. No. 16/517,012 filed Jul. 19, 2019, which is to issue as U.S. Pat. No. 10,820,577 on Nov. 3, 2020, the disclosure of which is hereby incorporated in its entirety by reference herein.

TECHNICAL FIELD

In at least one aspect, the present invention is related to collecting and distributing animal data via an unmanned aerial vehicle (UAV).

BACKGROUND

The continuing advances in the availability of information over the Internet have substantially changed the way that business is conducted. Simultaneous with this information explosion, sensor technology, and moreover, biosensor technology has also progressed. In particular, miniature biosensors that measure electrocardiogram signals, blood flow, body temperature, perspiration levels, or breathing rate are now available. Centralized service providers that collect and organize information collected from such biosensors to monetize such information do not exist. Moreover, access to and monitoring such sensors while individuals are in a designated location or engaged in certain activities such as sporting events present issues regarding accessibility.

Accordingly, there is a need for systems that collect and organize sensor data from an individual or groups of individuals during activities that require monitoring.

SUMMARY

In at least one aspect, an unmanned aerial vehicle-based data collection and distribution system is provided. The unmanned aerial vehicle-based data collection and distribution system includes a source of animal data that is electronically transmittable. The source of animal data includes at least one sensor. The animal data is collected from at least one target individual. The system also includes one or more unmanned aerial vehicles that receive the animal data from the source of animal data as a first set of received animal data, and a computing system (e.g., home station and/or a third-party platform and/or intermediary server) that is operable to receive at least a portion of the first set of received animal data. Characteristically, the one or more unmanned aerial vehicles include a transceiver operable to receive one or more signals from the source of animal data and to send one or more control signals to the source of animal data.

Advantageously, the methods and systems set forth herein have applications in sports/fitness, general wellness monitoring, military, risk mitigation industries, and the like.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements and wherein.

DETAILED DESCRIPTION

Figure 1:
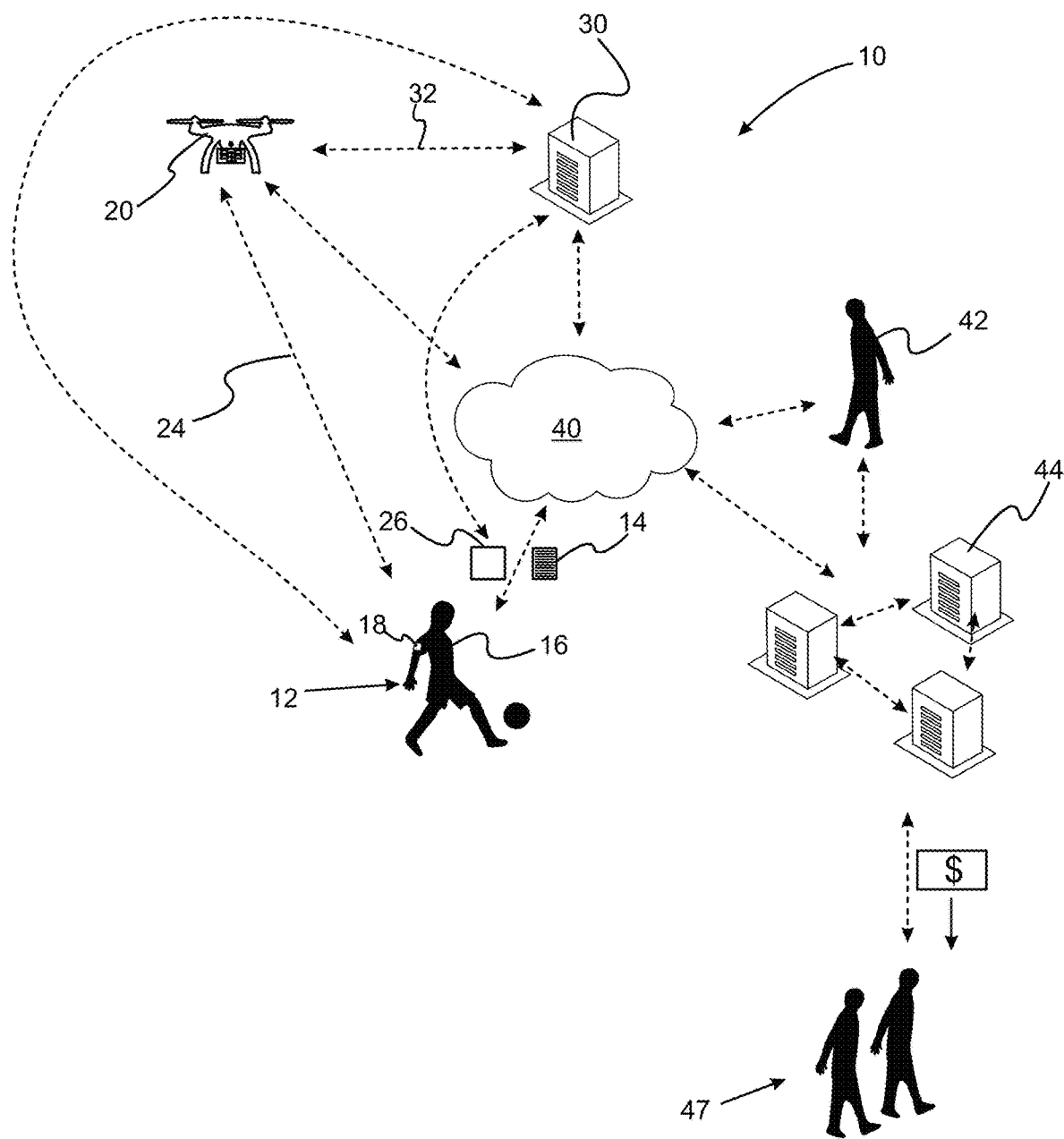
FIG. 1 is a schematic of a system for collecting and distributing animal data with an unmanned aerial vehicle.

Reference will now be made in detail to presently preferred embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural references unless the context clearly indicates otherwise. For example, a reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

Throughout this application, where publications are referenced, the disclosures of these publications in their entireties are hereby incorporated by reference into this application to more fully describe the state of the art to which this invention pertains.

When a computing device is described as performing an action or method step, it is understood that the computing device is operable to perform the action or method step typically by executing one or more line of source code. The actions or method steps can be encoded onto non-transitory memory (e.g., hard drives, optical drive, flash drives, and the like).

The term "computing device" generally refers to any device that can perform at least one function, including communicating with another computing device.

The term "server" refers to any computer, computing device, mobile phone, desktop computer, notebook computer or laptop computer, distributed system, blade, gateway, switch, processing device, or a combination thereof adapted to perform the methods and functions set forth herein. A server may be housed on an unmanned aerial vehicle.

The terms "subject" or "individual" refers to a human or other animal, including birds and fish as well as all mammals such as primates (particularly higher primates), horses, birds, fish sheep, dogs, rodents, guinea pigs, pig, cat, rabbits, and cows.

The term "animal data" refers to any data obtainable from a subject that can be transformed into a form that can be transmitted (e.g., wireless or wired transmission) to a server or other computing device. Animal data includes any data that can be obtained from sensors, and in particular, biological sensors. Animal data also includes any descriptive data, genetic data, genomic data, auditory data or visually-captured data that can be manually entered or otherwise provided.

The term "sensor data" refers to the unprocessed or manipulated signal generated by a sensor. In some cases, sensor data may also include characteristics related to the sensor itself.

The term "insight" refers to descriptions that can be assigned to a targeted individual that describe a condition or status of the targeted individual. Examples include descriptions or other characterizations of stress level, energy level, and the like. Insights may be quantified by one or more numbers, a plurality of numbers, a graph, a lot, a color or other visual representation, or a verbal description (e.g., high stress, low stress) that are predetermined.

The term "computed asset" refers to one or more numbers, a plurality of numbers, metrics, insights, graphs, or plots that are derived from at least a portion of the raw animal data. The sensors used herein initially provide an electronic signal. The computed asset is extracted or derived, at least in part, from the electronic signals. The computed asset describes or quantifies an interpretable property of the one or more targeted individuals. For example, electrocardiogram signals can be derived or extracted from analog front end signals, heart rate can be derived or extracted from electrocardiogram signals, body temperature can be derived or extracted from temperature sensors, perspiration levels can be derived or extracted from a perspiration sensor, hydration may be calculated from an in-mouth saliva sensor, location coordinates can be calculated or extracted from GPS or RFID data, biomechanical movement can be calculated or extracted from translation sensors, and breathing rate can be calculated or extracted from respiration sensors. In a refinement, a computed asset can include one or more signals or readings from non-animal data sources as one or more inputs in its one or more computations.

Abbreviations

"BLE" means Bluetooth Low Energy.
"HALE" means high altitude long endurance.
"HAPS" means a high altitude pseudo-satellite. It may also be referred to as an atmospheric satellite.

"RPAS" means a remotely piloted aerial system.
"UAV" means an unmanned aerial vehicle.
"VTOL" means vertical take-off and landing.

With reference to FIG. 1, a schematic of a system for collecting and distributing animal data with an unmanned aerial vehicle is provided. UAV-based transmission system 10 includes a source 12 of animal data 14 that can be transmitted electronically. Targeted individual 16 is the subject from which corresponding animal data 14 is collected. In this context, animal data refers to data related to a subject's body obtained from sensors and, in particular, biosensors as set forth below in more detail. In many useful applications, the subject is a human (e.g., an athlete) and the animal data is human data. Therefore, source 12 of animal data includes at least one sensor 18. Characteristically, one or more unmanned aerial vehicles 20 communicate directly or indirectly with sensors 18.

In a refinement, the collected animal data has attached thereto individualized metadata including characteristics of the animal data, the origination of the animal data, and sensor-related data (including the type of sensor, operating parameters, etc.). One or more attributes of an individual from which the animal data originated or other attributes related to the sensor or data can be added to the metadata or associated with the animal data after the animal data is collected (e.g., height, age, weight, data quality assessments, etc.).

In another refinement, the metadata includes information documenting the one or more activities a targeted individual is engaged in while the animal data is collected. The metadata can be attached to the collected animal data by unmanned aerial vehicle 20 or another computing device as set forth below.

In a further refinement, unmanned aerial vehicle 20 can directly communicate wirelessly with sensors 18 via wireless links 24. In this regard, UAV-based transmission system 10 can utilize any number of communication protocols including, but not limited to, BLE, cellular, LoRa, Ant+, WiFi, and the like.

In yet another refinement, unmanned aerial vehicle 20 is able to communicate with the at least one sensor from the one or more individuals using one or more communication protocols. In a variation, the unmanned aerial vehicle is able to communicate with the at least one sensor from the one or more individuals using one or more communication protocols simultaneously. For example, an individual may be wearing two separate sensors that transmit utilizing different communication protocols (e.g. BLE and Ant+), and the UAV can communicate with both sensors simultaneously by utilizing the primary method of communication found on each of the sensors.

In another refinement, source 12 includes computing device 26 which mediates the sending of animal data 14 to unmanned aerial vehicle 20, i.e., it collects the animal data and transmits it to unmanned aerial vehicle 20. For example, computing device 26 can be a smartphone, smartwatch, tablet or a computer carried by or proximate to targeted individual 16. In a refinement, a single computing device 26 can mediate the sending of animal data from a plurality of data sources. In a refinement, computing device 26 can also be UAV 20.

In a variation, unmanned aerial vehicle(s) 20 communicate with one or more third-parties, intermediary servers, home servers or each other. For example, unmanned aerial vehicle(s) 20 communicate with home station 30 via communication link 32. Typically, the animal data is downloaded to a computing device such as home station 30, a third-party platform 42 and/or intermediary server 44. Therefore, in a refinement, the unmanned aerial vehicle 20 attaches the metadata to the animal data before transmitting to the home server. In another refinement, the unmanned aerial vehicle 20 attaches the metadata to the animal data before transmitting to a third-party or intermediary server, with commands for data distribution established by the home station. In another refinement, home station 30 attaches the metadata after receiving the animal data from unmanned aerial vehicle 20. Home station 30 can be a server, laptop, mobile device, tablet or other computing device. In this variation, a user selects a sensor and opens a control application for the sensor on a home station 30. Typically, the sensor has been previously integrated with the control application prior to communicating with the UAV. In a refinement, the sensor(s) 18 uses the control application and UAV's recognized/established communication protocols. In a variation, unmanned aerial vehicle 20 communicates with sensor(s) 18 and/or home station 30 via cloud 40.

In a variation, a direct link between a target individual and the home station may be established in a localized network without accessing cloud 40. For example, individual 12 may establish direct communication between sensor 18 and home station 30 by opening up the control application on home station 30 to set up the sensor. In this case, the home station 30 may establish direct communication between UAV 20 and sensor 18. In another example, individual 12 establishes communication between sensor 18 and computing device 26 via a control application on computing device 26 to set up the sensor 18. Computing device 26 could then communicate with home station 30 directly to create a local network or communicate with home station 30 via cloud 40.

In another variation, one or more unmanned aerial vehicles 20 can receive data from one or more of the same sensors 18. Moreover, one or more unmanned aerial vehicles 20 can adjust their location or transceiver positioning based upon location of at least one sensor or one or more individuals.

In another variation, one or more unmanned aerial vehicles 20 is attached to or communicate with one or more apparatus devices. Examples of such devices include a satellite or equipment, perhaps but not necessarily in a stadium infrastructure.

In another variation, home station 30 monitors the one or more UAVs 20 and/or the at least one sensor, with an event occurring that either (1) alerts the home station, intermediary server, or third-party, and/or (2) prompts the home station to take at least one corrective action in furtherance of delivering an expected output to either the home station, intermediary server or third-party.

In another variation, UAV-based transmission system 10 communicates with a home station 30 or a third-party platform 42 and/or intermediary server 44, all which may occur either directly or via cloud 40. In the event UAV is not able to communicate with home station 30 or third-party 42 or intermediary server 44, or has been instructed to not send collected animal data to any end point, the unmanned aerial vehicle 20 may continue to collect and store animal data. The collected animal data will be transmitted when the connection to the home station or third-party system or intermediary server is reestablished, or when the one or more UAVs have been so instructed. In a variation, the one or more UAVs may be instructed to send at least a portion of the collected animal data from a sensor to a third-party, intermediary device, or home station while storing the collected animal data from the sensor on the UAV for possible use at a later time. In yet another variation, if the unmanned aerial vehicle is not able to communicate with the at least one sensor, the unmanned aerial vehicle may be programmed to reconnect with the at least one sensor automatically after one or more of parameters such as the following change: time, location of the at least one sensor, location of the one or more individuals, or location of the one or more UAVs. It will be appreciated that such parameters are merely exemplary and not exhaustive. Depending on the situation, other parameters may be deemed relevant. Location can include physical location or directional location of the UAV or any of its components, (e.g., the direction a transmission component on the UAV is pointing like an antenna). Additionally, automatic reconnection may occur via an instruction or series of instructions sent from the home station, or instruction or series of instructions that are pre-programmed on the UAV.

In a refinement, unmanned aerial vehicle 20, a plurality of unmanned aerial vehicles and/or home station 30 are operable to transform sensor data into an insight. It should be appreciated that home station 30 is a computing device that executes the control application while intermediary server 44 is a computing device that can receive the animal data with or without the metadata and attributes attached thereto. Moreover, intermediary server 44 can implement the same operations described herein as home station 30 regarding data processing.

In another variation, the unmanned aerial vehicle 20 and/or the home station 30 and/or intermediary server 44 are operable to assign one or more classifications to the animal data, the one or more classifications including metric classifications, insight classifications, data properties, data timeliness classifications, or data context classifications. Additional details of classifications and their association with the animal data are disclosed in U.S. Pat. No. 62/834,131 filed Apr. 15, 2019; the entire disclosure of which is hereby incorporated by reference.

In still another variation, the animal data is distributed to one or more third-parties or target individuals for consideration. In this regard, stakeholders 47 will receive consideration for the animal data (e.g., payment, and/or a trade for something of value). In a refinement, consideration may be non-monetary so long as it is of some value to one or both parties. For example, a stakeholder may agree to provide a third-party analytics company with their animal data in exchange for obtaining insights related to the stakeholder. This transaction can be monitored by home station 30, intermediary server 44, or other monitoring systems.

In still another variation, sensor data is sent from the UAV to one or more end points, including a control application for the UAV-based transmission system 10 (e.g., running on a computer such as home server 30, computing device 26, or the like), its cloud 40, or a third-party 42 (e.g., hospital, insurance provider, broadcaster, sports wagering platform, smartwatch, health and wellness monitoring system).

In yet another variation, home station 30 monitors the one or more UAVs and/or at least one sensor, with an event occurring that either (1) alerts the one or more home stations, intermediary servers, or third-parties, and/or (2) prompts the home station to take at least one corrective action in furtherance of delivering an expected output to one or more of the home station, intermediary server, or third-party. For example, the system may be capable of monitoring the UAVs and take corrective actions related to error conditions and failure. If the connection between sensor and UAV is weak or the UAV has a power issue (e.g., battery degradation), a corrective action instructed by the home station may be for a new UAV to travel and replace the faulty UAV that is currently being utilized to transmit from sensor to home station, intermediary server, or third-party. In a variation, the home station may instruct the UAV being replaced to communicate with the replacement UAV to ensure it is taking over specific UAV-related duties for that UAV (e.g., connecting with a specific sensor(s), being a relay hub in a specified network, etc.) and provide the new UAV with access to the relevant information (e.g., historical data, algorithms, integrations with data endpoints) to ensure replacement is seamless. In another example, if a UAV determines that at least one sensor is bad and the UAV cannot connect or reconnect, an automated trigger may occur whereby a backup UAV is deployed to try and connect with the sensor, or the UAV sends an alert to the central server that the sensor needs to be replaced. In yet another example, the UAV may detect a health or medical condition based upon the collected animal data, which may trigger either an alert or at least a portion of the collected animal data being sent by the UAV to the one or more home stations, intermediary devices or third-parties.

Figure 2:
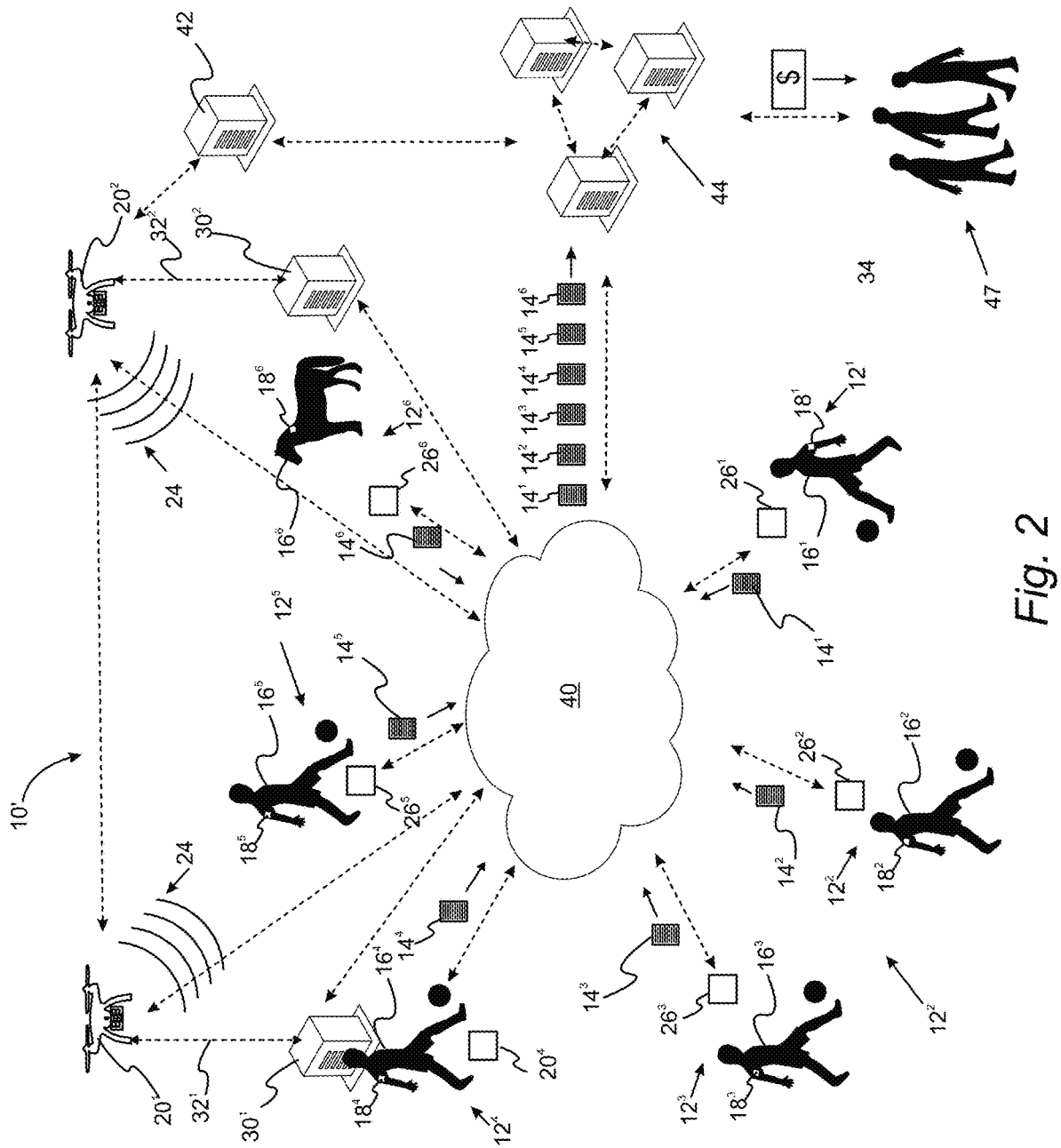
FIG. 2 is a schematic of an unmanned aerial vehicle-based transmission system using multiple sensors acquiring sensor data from multiple targeted individuals.

FIG. 2 provides a schematic of an UAV-based transmission system using multiple sensors acquiring sensor data from multiple targeted individuals. This variation illustrates a scenario applicable to a sporting event in which there is a plurality of targeted individuals (e.g., athletes). UAV-based transmission system $10'$ includes a sources $12^i$ of animal data $14^i$ that can be transmitted electronically. Targeted individual $16^i$ is the subject from which corresponding animal data $14^i$ is collected. In this context, animal data refers to data related to a subject's body derived from sensors and, in particular, biosensors as set forth below in more detail. In many useful applications, the subject is a human (e.g., an athlete) and the animal data is human data. Therefore, source $12^i$ of animal data includes at least one sensor $18^i$. In this context, "i" is merely a label to differentiate between different targeted individuals, sources, sensors, and animal data. It should be appreciated that the present embodiment is not limited by the number of different targeted individuals, sources, sensors, and animal data. Characteristically, unmanned aerial vehicles $20^j$ communicate with sensors $18^i$. In this context, "j" is an integer label differentiating the multiple unmanned aerial vehicles. It should also be appreciated that the present invention is not limited by the number of unmanned aerial vehicles. In one refinement, unmanned aerial vehicles $20^j$ can directly communicate wirelessly with sensors 18 via wireless links 24. In this regard, UAV-based transmission system or network $10'$ can utilize any number of communication protocols including, but not limited to, BLE, LoRa, cellular, Ant+, WiFi, and the like. In a variation, the unmanned aerial vehicle is able to communicate with the at least one sensor from the one or more individuals using one or more communication protocols simultaneously. For example, an individual may be wearing two separate sensors that transmit utilizing different communication protocols (e.g., Bluetooth and Ant+), and the UAV can communicate with both sensors simultaneously by utilizing the primary method of communication found on each of the sensors. In a refinement, the collected animal data has attached thereto individualized metadata including characteristics of the animal data, the origination of the animal data, and sensor-related data (including sensor type, operating parameters, etc.). Some attributes of an individual from which the animal data originated or other attributes related to the sensor or data can be added to the metadata or associated with the animal data after the animal data is collected (e.g., height, age, weight, data quality assessments, etc.). In a refinement, the metadata includes the activity a targeted individual is engaged in while the animal data is collected. In another refinement, source 12 includes computing device 26 which mediates the sending of animal data 14 to unmanned aerial vehicles 20, i.e., it collects the animal data and transmits it to unmanned aerial vehicle 20. For example, computing device 26 can be a smartphone, smartwatch, tablet or a computer carried by or proximate to targeted individual $16^i$. It can also be on, in, or as part of a UAV. It should be appreciated that the unmanned aerial vehicles $20^j$ can communicate with each other and exchange information (e.g., sensor signals).

As set forth above, unmanned aerial vehicles $20^j$ communicate with home station $30^j$ via communication links $32^j$. In a variation, a single home station can interact with multiple unmanned aerial vehicles $20^j$, either to create a single network or a plurality of networks. In a variation, a network that includes a home station, at least one sensor, and one or more unmanned aerial vehicles provides an ability to encrypt or compress data being stored or transmitted to or from the at least one sensor, home stations, or unmanned aerial vehicles. In another variation, a network that includes a home station, at least one sensor, and one or more unmanned aerial vehicles provides an ability to obfuscate any data being transmitted to/from the one or more sensors, home station, or unmanned aerial vehicles. Typically, the animal data is downloaded to home station $30^j$. Home station $30^j$ is a computing device such as a server, laptop, mobile device, tablet, a programmable logic array (e.g., a field-programmable logic array) and the like. In this variation, a user selects a sensor and opens a control application for the sensor on a home station $30^j$. Typically, the sensor(s) $18^i$ have been previously integrated with the control application running on home station $30^j$ prior to communicating with the UAV. In a refinement, the sensor(s) $18^i$ uses the control application and UAV's recognized/established communication protocols. In another variation, unmanned aerial vehicle $20^j$ communicates with sensor(s) $18^i$ and/or home station $30^j$ via cloud 40.

In another variation, UAV-based transmission system $10'$ communicates with a home station 30 or a third-party platform 42 (collectively "third-party 42") and/or intermediary server 44 via cloud 40. In the event UAV is not able to communicate with home station 30 or third-party 42 or intermediary server 44, the unmanned aerial vehicle $20^j$ may continue to collect and store animal data. In a refinement, if the unmanned aerial vehicle is not able to communicate with the at least one sensor, the unmanned aerial vehicle may be programmed to reconnect with the at least one sensor automatically after one or more of the following exemplary parameters change: time, location of the at least one sensor, location of the one or more individuals, or location of the one or more UAVs. Automatic reconnection may occur via a control command sent from the home station, or the UAV is programmed to automatically reconnect. The collected animal data will be transmitted when the connection to the home station or third-party system or intermediary server is reestablished. In a refinement, unmanned aerial vehicle $20^j$ and/or home station $30^j$ is operable to transform at least a portion of the sensor data into an insight or further manipulated data.

In a refinement, UAV 20 can serve as an extension of an existing sensor communication with home station 30. In a variation, one or more communications between at least one sensor and home station 30 is "handed off" from a non-unmanned aerial vehicle transmission system to one or more UAVs, and vice versa, within a network or a plurality of networks. For example, if a sensor is communicating with home station 30 via a computing device's internal transmission system (e.g., smartphone using Bluetooth) and the computing device ceases transmission from a sensor to the home network, the UAV may have the ability to detect that a connection has been lost between sensor and computing device and start communication between sensor and UAV, enabling the UAV to serve as an extension between the sensor and the home station, intermediary server, or third-party. Once the sensor has been "handed off" from the computing device to the one or more UAVs, the home station may update the one or more UAVs regarding all required characteristics related to the sensor, the animal data, the individual, and the required one or more outputs. In a variation, the UAV "hands off" sensor communication to the computing device in the event the sensor is not able to communicate with the UAV (e.g., if the individual is in a tunnel or area where there is no reception).

With reference to FIG. 2, one or more unmanned aerial vehicles 20 can communicate with one or more third-parties 42, intermediary servers 44, home stations 30, or each other, thus enabling sharing of data, sharing of home sensor duties, or sharing of other information across UAVs within a single network or a plurality of networks. In a refinement, multiple UAVs 20 may have the ability to communicate with a single third-party 42, intermediary server 44, or home station 30. Alternatively, a single UAV may have the ability to communicate with multiple third-parties 42, intermediary servers 44, or home stations 30. In a refinement, an intra-UAV communication network can be created, with one or more unmanned aerial vehicles acting within a single network or independently of each other, with one or more home stations communicating with one or more unmanned aerial vehicles, and two or more unmanned aerial vehicles 20 communicating with each other.

In a variation, one UAV 20 may act as a primary server and data collection point with one or more UAVs 20 acting as extensions of the primary UAV within a single network, a plurality of networks, or independently of each other. In a refinement, one or more home stations communicate with one or more unmanned aerial vehicles, and two or more unmanned aerial vehicles communicate with each other.

In another variation, the one or more UAVs communicate solely with the primary UAV which in turn communicates with the home station, intermediary server, or third-party on behalf of all UAV's within a given network.

In another refinement, one or more unmanned aerial vehicles 20 take one or more coordinated actions on at least a portion of the same data set based upon one or more commands sent by a home station 30. For example, UAV1 may collect the animal data and attach metadata, and UAV2 may access the animal data from UAV1 to provide analysis on the collected animal data with its associated metadata. In a variation, one UAV may collect the animal data and attach metadata to the collected animal data, and send a portion of the collected animal data to another UAV for analysis while storing a portion of the collected animal data for download use at a later date. In yet another refinement, the one or more unmanned aerial vehicles may be programmed to receive data from one or more of the same sensors.

An example of unmanned aerial vehicle 20 of FIGS. 1 and 2 is an aircraft that is piloted by remote control or autonomous onboard computers, without an onboard human presence. Examples include a high-altitude long-endurance aircraft, a high altitude pseudo satellite, an atmospheric satellite, a balloon, a multirotor drone, or a fixed-wing aircraft. More specific examples of fixed-wing aircraft include HALE, multirotor, and other fixed-wing aircraft. Other names used interchangeably with UAV are RPAS and Drone. Another example of a UAV is a HALE/HAPS, which is an aircraft that flies at high altitudes (e.g., in Class A airspace over the U.S.—18000 ft MSL to 60,000 ft MSL—or near orbital) above most weather and commercial air traffic. These aircraft may be designed for long flight times, ranging from 3-4 months at a time without landing. Some have the capabilities to stay aloft for years without the need to land or refuel. Due to their requirement to stay aloft for weeks, months, or years at a time, solar power is essential to recharge the batteries on a daily basis. Examples include geostationary balloon satellites or other plane-based atmospheric satellites. Another example is a multirotor. Multirotor aircraft are the most popular types of small drones and have 2 or more rotors. The rotors allow it to function like a helicopter. These types of drones have a very smooth and precise flight path. However, these devices have a very high power draw and little surface area for solar cells. As a result, their flight times are typically limited to under an hour, although battery life and its impact on resulting flying time continue to increase. Another example is a VTOL device. These devices can take off and land vertically, with the ability to hover mid-flight. VTOL devices are most commonly of the multirotor design. Some newer VTOLs are hybrid multirotor/fixed wing aircraft that can take off and land vertically using multiple rotors but then transition to horizontal flight using wings and a propeller. Additional specific examples of drones include, but are not limited to, Airbus Zephyr S, Airbus Zephyr T, Aurora Odysseus, Raven Aerostar STRATOSPHERIC AIRSHIPS, Raven Aerostar THUNDERHEAD BALLOON SYSTEMS, AeroVironment HAWK30, AeroVironment Global Observer, Astigan A3, General Atomics MQ-9 Reaper, Ukrspecsystems PC-1 Multirotor Drone, Ukrspecsystems PD-1 VTOL, Ukrspecsystems PD-1 Fixed Wing, DJI Mavic 2 Enterprise Drone, and DJI Phantom 4 Pro V2.0.

Figure 3:
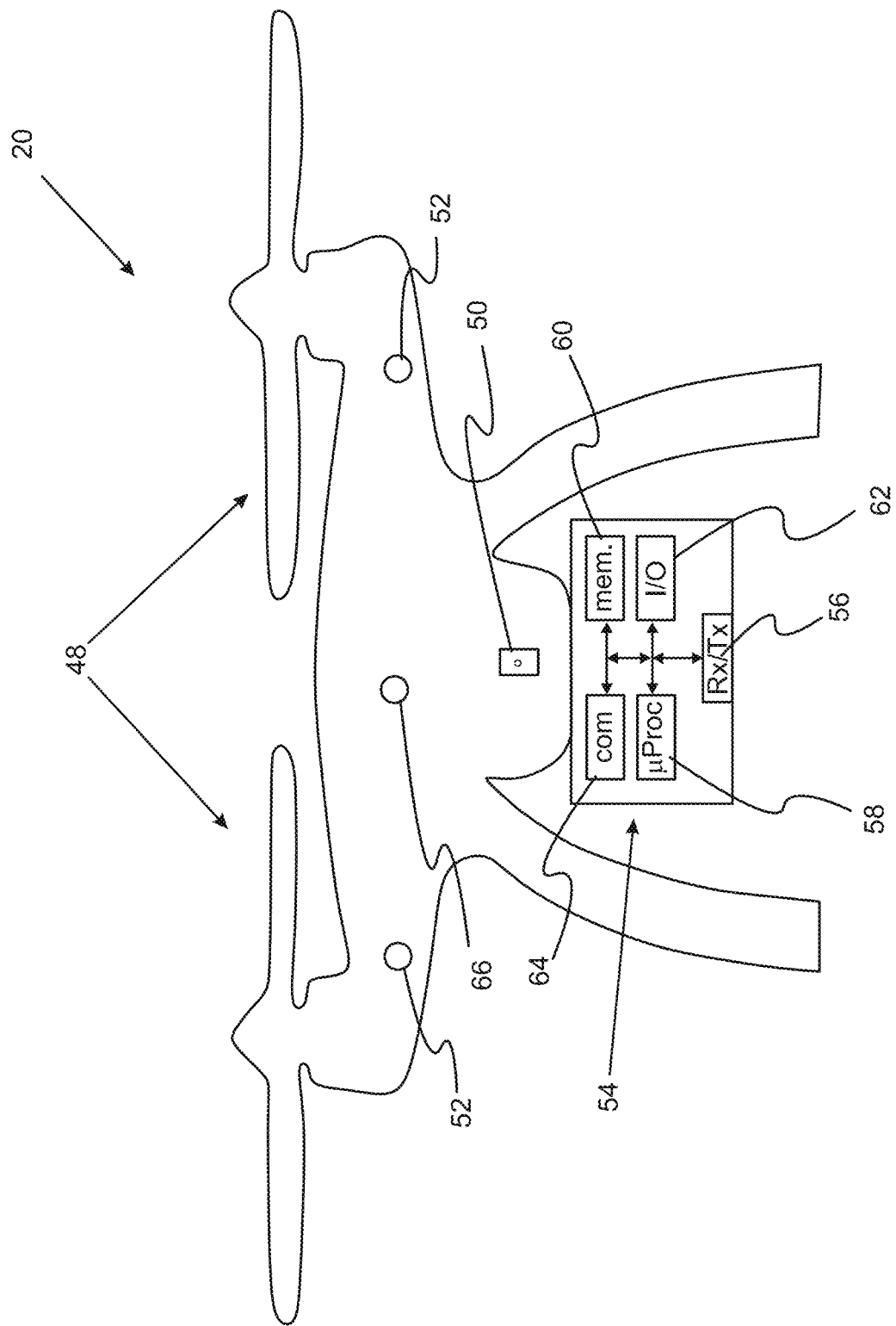
FIG. 3 is a schematic of an unmanned aerial vehicle with an integrated computing device.

FIG. 3 depicts a schematic of a variation of an unmanned aerial vehicle that can be used in UAV-based transmission system 10. Unmanned aerial vehicle 20 includes aerial propulsion system 48 which will depend on the particular design of the unmanned aerial vehicle. In a refinement, unmanned aerial vehicle 20 includes camera 50 which can be used to provide one or more videos (e.g., streaming media) or photographs, which may be accompanied by audio and other data from the same camera, of targeted individual 16, spectators, or the proximate area thereof. In a refinement, unmanned aerial vehicle 20 can include optical trackers 52 (e.g., tracking the location of target individual 16), weather trackers (e.g., wind, temperature, humidity), or other technologies integrated therein. Unmanned aerial vehicle 20 includes data acquisition unit 54 that communicates with the sensors 18. In a refinement, unmanned aerial vehicle 20 includes transceiver module 56 that communicates with sensors 18. This communication is typically via a two-way communication link in which a user can activate and set parameters for the sensors and received data signals from the sensors. In a refinement, transceiver module 56 can also be used to communicate with third-party 42 and/or intermediary server 44. In another refinement, transceiver module 56 is operable to receive one or more signals from the source of animal data and to send one or more control signals to the source of animal data, e.g., inject more insulin, turn off a sensor, stream data when a command is given, etc. Typically, the ability to send will be a command from the home station, which will control unmanned aerial vehicle 20.

In some variations, data acquisition unit 54 can also include microprocessor 58, which is in electrical communication with memory module 60 and input/output module 62. Microprocessor 58 can be operable to execute one or more data processing steps, examples of which are set forth below. In a refinement, data acquisition unit 54 includes communication module 64 which allows communication via one or more protocols (e.g., Ant+, BLE, LoRa, WIFI or via a cellular connection or combinations thereof).

In another variation, one or more unmanned aerial vehicles 20 have attached, affixed, or embedded at least one sensor 66 on the UAV that capture one or more data points and either (1) relay at least a portion of the animal data to either the home station and/or a third-party or intermediary server, or (2) use at least a portion of the captured animal data to transform at least a portion of captured sensor animal data into an insight or metric.

It should be appreciated that UAV-based transmission system 10 processes acquired animal data into a form for distribution and, in particular, perhaps (but not necessarily) into a form for monetization. In this regard, data acquisition unit 52 collects the animal data from sensors 18. Data acquisition unit 52 is operable to execute one or more steps such as but not limited to normalizing, time stamping, aggregating, storing, manipulating, enhancing, organizing, analyzing, anonymizing, summarizing, synthesizing, bookkeeping, synchronizing or distributing the animal data over longer distances from at least one sensor to the home station or a third-party system (e.g., user watch, user phone, health, and wellness system, media/sports betting system).

As set forth above, the UAV-based transmission system includes sensors, and in particular biosensors. Biosensors collect biosignals, which in the context of the present embodiment are any signals in animals that can be continually measured and monitored, including both electrical and non-electrical signals. In a refinement, the biosensor can be a system that outputs facial recognition data or auditory data. A biosensor can gather physiological, biometric, chemical, biomechanical, genetic, genomic, location, or other biological data from a targeted individual. For example, some biosensors may measure physiological metrics such as, biosignals, bioelectrical signals, blood flow, blood analysis, core body temperature, blood pressure, biological fluid, pulse, oxygenation, skin temperature, perspiration levels, glucose levels, hydration levels, lactate levels, sodium levels, potassium levels, heart rate, genetic information, muscle activity, or breathing rate. Some biosensors may detect biomechanical metrics such as, for example, angular velocity, joint paths, or position or accelerations in various directions from which a subject's movements may be characterized. Some biosensors may detect location coordinates and data (e.g., GPS, RFID), facial recognition data, skeletal data, physical pressure (e.g., captured from a sensor located at the bottom of a shoe), or audio data related to the one or more target individuals. In addition to biological data about the targeted individual, some biosensors may measure environmental conditions such as ambient temperature and humidity, elevation, barometric pressure, other audio, and other location. Specific examples of biosensors include, but are not limited to, Mc10 BioStamp nPoint (ECG+sEMG+XYZ coordinates), ECG: Vivalnk Vital Scout (ECG); Humon Hex (muscle oxygen); Apple Watch (heart rate); Polar H10 chest strap (heart rate and HRV); 23 and me (DNA/genetic testing); nebula genomics (genomic testing); NEC NeoFace Watch (facial recognition); Auditory: Sonitus technologies MolarMic (auditory); SennoFit Insole (gait analysis); Omron HeartGuide Wearable Blood Pressure Monitor, model: BP-8000M (blood pressure); Glucose: Abbott freestyle Libre (glucose); Health Care Originals ADAMM (respiration); Epicore Biosystems (hydration/sweat analysis); Kenzen Echo Smart Patch (hydration/sweat analysis); IsoLynx Athlete Tracking Tags and Wireless Smart Nodes (RFID-based location tracking); Catapult OptimEye S5 (location tracking (GPS)); SMRT Mouth (biometric mouth guard); StrikeTec (biomechanical movement sensors for fight sports); Scanalytics (smart floor sensors); and Lockheed Martin FORTIS industrial exoskeleton products (biomechanical movements). In a refinement, the at least one sensor $18'$ is affixed to, or is in contact with, a subject's body, eyeball or skeletal system (e.g., saliva sensor affixed to a tooth, set of teeth, or an apparatus that is in contact with one or more teeth), embedded in a subject, lodged in a subject, ingested by a subject, or integrated as part of, affixed to, or embedded within, a fabric, textile, cloth, material, fixture, object, or apparatus that contacts or is in communication with a target subject either directly or via one or more intermediaries. Examples include a sensor integrated or embedded into a shirt, a sensor integrated or embedded into a shoe that may contact the individual through the intermediary sock and adhesive tape wrapped around an individual's ankle. In another refinement, sensors may be embedded into, integrated with, or affixed to the floor or ground (e.g, basketball floor, soccer field), a seat/chair, helmet, or an object that is in contact with the subject either directly or via one or more intermediaries (e.g., a subject is in contact with a sensor in a seat via a clothing intermediary).

The UAV-based transmission system may also have attached, affixed, or embedded at least one sensor on the UAV that capture one or more data points (e.g., wind speed, temp, humidity, UV %, animal recognition, other audiovisual information) and (1) relay at least a portion of the animal data to either the home station and/or a third-party or intermediary server, and/or (2) use at least a portion of the captured animal data to transform captured sensor data into processed data (e.g., an insight or metric). For example, the UAV may have attached, affixed, or embedded sensors that utilize facial recognition software to capture emotion from one or more targets. The UAV may then utilize the collected sensor data from the individual to correlate the facial recognition data with the collected animal data (e.g., ECG data that can provide heart rate variability) to determine the "stress" level of an individual at any given time.

With reference to FIGS. 1 and 2, UAV-based transmission system 10 or 10' can communicate in real time or near real-time with home station 30 and/or third-party 42 and/or intermediary server 44 for example, during a sporting event or activity. Therefore, third-party 42 can be a broadcaster of a sporting event, an application for spectators, a coach/trainer of a physical activity, an airline monitoring its pilots, a hedge fund monitoring its traders, a construction site monitoring its workers, a hospital monitoring outpatients, an army monitoring its soldiers, or a variety of other use cases. UAV-based transmission system 10 can operate as an intermediary hub in which the UAV 20 collects sensor data and the control application executing on a computing device will have the ability to execute various commands on the UAV, including commands such as: (1) streaming at least a portion of the collected animal data in real time or near real time back to the control application, intermediary server, or third-party platform; (2) selecting one or more data streams to be sent back to the control application, intermediary server, or third-party system; (3) selecting a frequency upon which data is sent back to the control application, intermediary server, or third-party system; (4) transforming at least a portion of the collected animal data on the unmanned aerial vehicle to a computed asset, with the collected animal data being from the at least one sensor, and sending one or more computed assets to the control application, intermediary server, or third-party system; (5) aggregating one or more data streams on the unmanned aerial vehicle from at least one sensor to create one or more transformed data that can be sent back to the control application, intermediary server, or third-party system; (6) changing or adjusting the settings within the at least one sensor; (7) instructing the at least one sensor to perform an action; (8) changing or adjusting the location of the one or more unmanned aerial vehicles; and/or (9) storing sensor data.

Figure 4A:
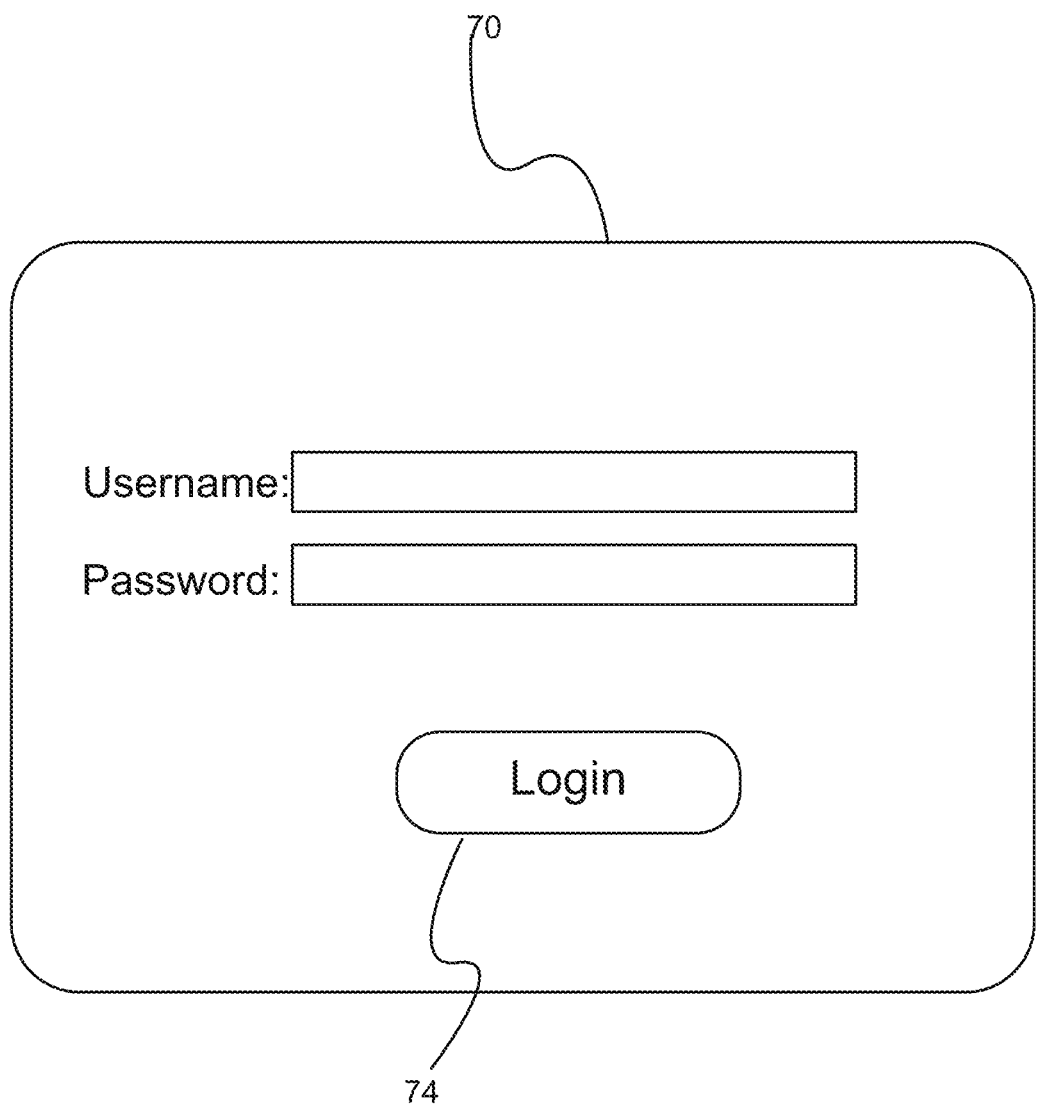
FIGS. 4A, 4B, and 4C are illustrations of a user interface for operation of the unmanned aerial vehicle-based transmission system.
Figure 4B:
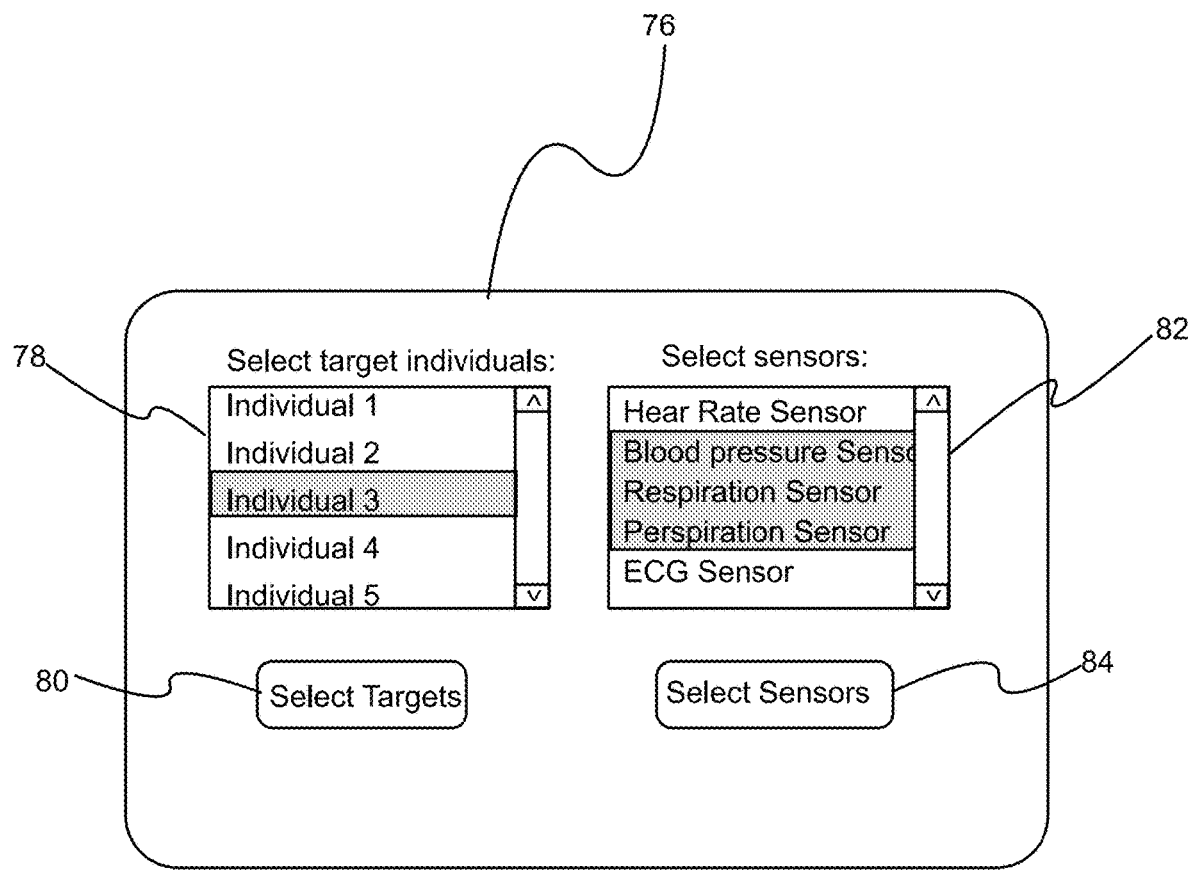
Figure 4C:
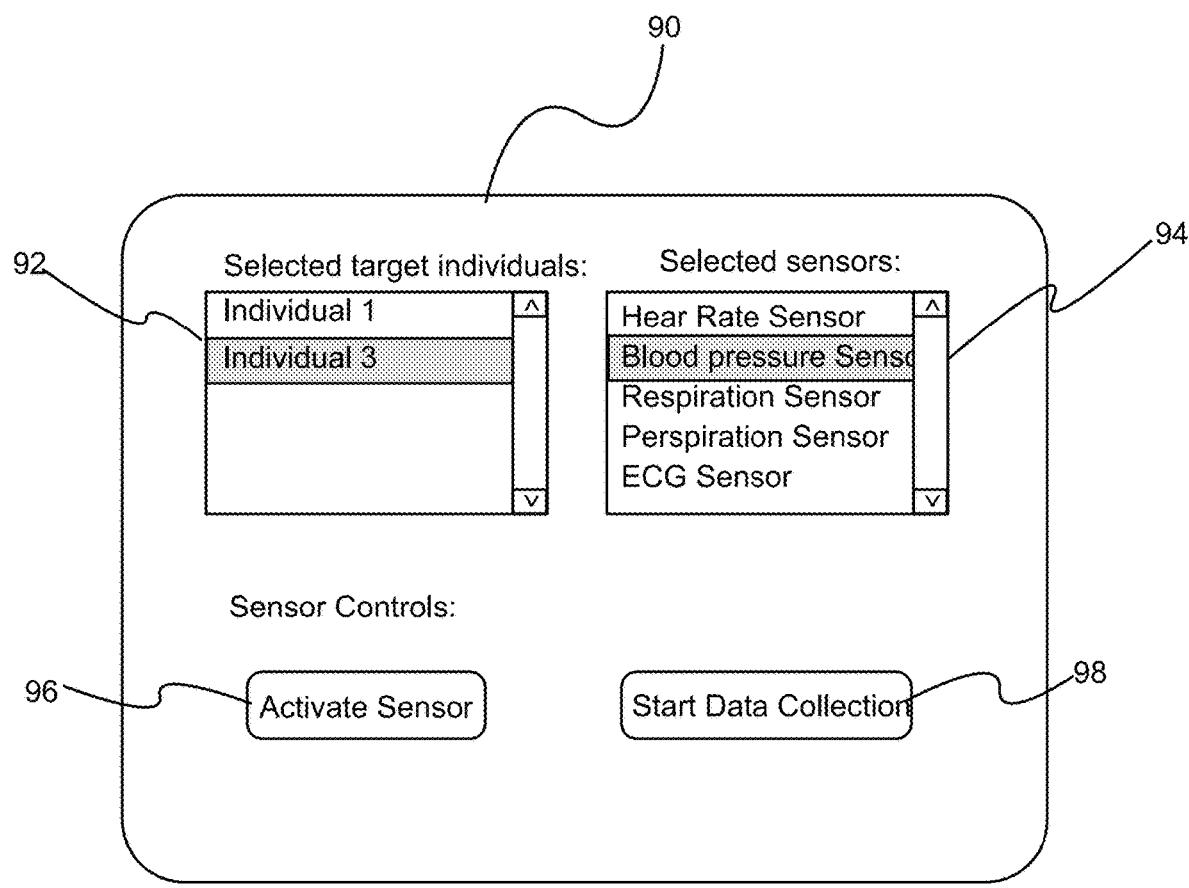

In some variations, the control application will have the ability to set up, control some or all functionality, and configure the one or more unmanned aerial vehicles through the single application. Depending on the unmanned aerial vehicle or the established network of UAVs, the UAV or network of UAVs may be operated via the control application or remotely through a third-party control. Once communication is established between sensor and UAV or network of UAVs, the UAV or network of UAVs will act in one or more of three roles: (1) an extension of the home station to facilitate communication between the sensor(s) and the home station or a third-party system over long distances; (2) an intermediary hub that communicates with the sensor(s), receives sensor data, processes data, stores data, and sends data over longer distances to the home station or a third-party system (e.g., a user watch, phone, health and wellness platform); or (3) acting as the home station. It will have the capability to normalize, time stamp, aggregate, store, manipulate, enhance, organize, analyze, anonymize, summarize, synthesize, bookkeep, synchronize and distribute data, as well as create and disseminate commands. Commands can be sent and received from the control application to the sensor via the UAV. This means the control application will be able to set up, control, configure and operate all sensors via communication through the UAV. Commands can be sent and received from the control application to the UAV for any number of sensors With reference to FIGS. 4A, 4B, and 4C, illustrations of a user interface for operation of the UAV-based transmission system 10 are provided. A user logs into the control application via user interface 70 typically by entering a "username" and "password" and then actuating control element 74. Interface 76 is then presented to the user from which displays list box 78 showing a list of target individuals that can be selected for monitoring. The user can select one or more individuals to monitor. Control element 80 finalizes the selection. The user then chooses at least one sensor from sensor list box 82 associated with the selected individual. It should be appreciated that a sensor may capture more than one metric. For example, a sensor that captures ECG may also have an accelerometer, gyroscope, and magnetometer in it to capture X, Y, Z coordinates. Control element 84 finalizes the selection.

With reference to FIG. 4C, after selecting the target individuals and sensors, user interface 90 is displayed. The user identifies which of the selected sensors are to be operated. This is accomplished by highlighting the selected one or more target individuals in list box 92 and the sensor in list box 94 powers the sensor(s) "on" via control element 96 if required. In a refinement, target individuals in list box 92 may be grouped together so that a user can select a category of users rather than individual users. The user then can place sensor(s) on his/her body if he/she is a target individual. The user then actuates a start data collection control element 98 for each sensor utilized by user to start collecting data. Once the sensor is started, the user can locate all UAVs either within range via the control application. Alternatively, the user can locate all UAVs within the parameters of the user activity (e.g., user is going on a 100 mile bike race which goes along a specific path), and select what UAV it would like to pair with. In a variation, the home station will ping all UAVs within a range or network to automatically select and connect with the best-suited UAV for the at least one sensor to connect with. In another variation, the UAVs within a given location or range can automatically detect the at least one sensor and determine which UAV or network of UAVs the at least one sensor should pair with. In yet another variation, the UAVs can be configured to enable the at least one sensor to switch communication from one UAV to another if the at least one sensor or individuals change location or other issues that affect sensor or UAV communication arise (e.g., signal strength, signal quality). Each of control elements in FIGS. 4A, 4B, and 4C are depicted as "buttons." It should be appreciated that for each of the control elements depicted in FIGS. 4A, 4B, and 4C, control elements such as selection boxes, dropdown lists, buttons, and the like can be used interchangeably.

In a refinement, the home station can be programmed to automatically select the one or more UAVs to connect with the at least one sensor based on one or more of following characteristics: unmanned aerial vehicle location, unmanned aerial vehicle payload, unmanned aerial vehicle bandwidth, individual location, sensor location, battery life, signal strength, environmental conditions, or signal quality. In another refinement, the network of the home station, the at least one sensor and the one or more unmanned aerial vehicles provide an ability to monitor one or more characteristics related to the at least one sensor, the sensor signal, or collected animal data, and take an action to maintain optimal communication between the home station, the at least one sensor, the one or more UAVs, the one or more intermediary servers, and the one or more third-parties. For example, the network may provide an ability to monitor signal connection strength and signal quality across all potential data transfer points, as well as enabling the home station to automatically select and change the best communication/data transfer point within the network, which may be another unmanned aerial vehicle, intermediary server or other transmission mechanism. In a variation, the network may switch sensor communication from one UAV to another UAV based upon a desire to maintain or increase sensor signal strength. In another refinement, the home station (1) detects and monitors one or more characteristics related to the signal quality and signal strength between the at least one sensor and one or more UAVs across one or more data communication points, and (2) provides one or more commands to the sensor to pair with a secondary transmission source which may be another UAV or other non-UAV transmission system. In a variation, the home station provides one or more commands that enables the at least one sensor to alternate which UAV the at least one sensor communicates with based upon feedback provided to the home station or intermediary server by the one or more UAVs related to signal strength, signal quality, UAV battery life, or other relevant considerations.

In some variations, a network consisting of a home station, at least one sensor and one or more unmanned aerial vehicles may provide an ability to encrypt or compress data being stored or transmitted to or from the at least one sensor, home stations, or unmanned aerial vehicles. In some variations, a network consisting of a home station, at least one sensor, and one or more unmanned aerial vehicles provide an ability to obfuscate any data being transmitted to/from sensors, home station, or unmanned aerial vehicles.

As set forth above, the user can pair multiple sensors to a single UAV at the same time within the control application, or pair multiple sensors to multiple UAVs. Once the appropriate UAV is selected, the user then enables a pairing function between sensor and UAV. This pairing function may initiate immediately if the sensor is in range of the UAV or initiate when the sensor is in range of the UAV. Alternatively, the sensor may transmit first to the control application and then handoff to the UAV if the sensor is able to pair with multiple transmission systems (e.g., broadcast network).

In another refinement, multiple UAVs can communicate with a single sensor (e.g., in the event that a single UAV covers a specific area) if the UAV is assigned to a specific area (and the user goes outside that area) based on the control application. In another refinement, multiple sensors may communicate with a single UAV (in the event, there are multiple people using a single UAV or a single person is wearing multiple sensors). In other refinements, multiple UAVs can be utilized at the same time and with the same one or more sensors, and the UAVs will have the ability to communicate with each other. For example, as part of a mesh network, the UAV system which has the ability to switch from one to the next UAV if the subject moves out of range (assuming the UAV is responsible for covering a specific area), or other needs require it (e.g., bandwidth).

The elevation at which the unmanned aerial vehicle can "sit" (e.g., hover) can vary. For example, the unmanned aerial vehicle can be a high-altitude pseudo satellite, which flies in high altitudes above weather and commercial air traffic. These aircraft are typically designed for long flight times, ranging from 3-4 months at a time or even upwards of multiple years without landing. HAPS can also be utilized a link between drones flying close to the earth's surface or another system and satellites orbiting in space. Additionally, HAPS could be useful as an intermediate relay step between a satellite and a ground station, supporting the transfer of data and reducing the ground and satellite infrastructure required. HAPS efficiently complement the networks where the target area is limited and changing and where ground infrastructure is nonexistent or unavailable.

In some variations, the UAVs may utilize solutions for longer-term battery life, including solar-powered charging. In a variation, one UAV may be attached to another UAV (e.g., satellite). In another variation, the UAVs may also not need to be aerial and could be affixed to stationary or movable objects (e.g., an apparatus in a stadium or arena). The UAVs may also be connected via cable (e.g., Ethernet, fiber) to stationary objects for faster connectivity.

In a variation, the one or more UAVs can detect the location or positioning of the at least one sensor or one or more individuals, and the one or more UAVs can adjust their location or transceiver positioning based upon the location of the at least one sensor or one or more individuals. For example, if a UAV is tracking a group of people, and the group of people moves to a new location, the UAV may change its location or adjust its transceiver positioning to ensure optimal data transfer and collection between the at least one sensor and the UAV. In a variation for sporting applications, subject to Federal Aviation Regulations, one or more UAVs can sit over a stadium (e.g., football, baseball, soccer) or racetrack and act as a transmission hub for all players on a field. In other sporting applications, the UAV can follow a cycling race (and specifically the participants).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An unmanned aerial vehicle-based data collection and distribution system comprising:
   a source of animal data that is electronically transmittable, the source of animal data including at least one sensor, the animal data being collected from at least one target individual;
   an unmanned aerial vehicle that receives the animal data from the source of animal data as a first set of received animal data, the unmanned aerial vehicle having a transceiver operable to receive one or more signals from the source of animal data and to send one or more control signals to the source of animal data;
   a computing device that is operable to receive at least a portion of the first set of received animal data; and
   a monitoring system that is configured to monitor distribution of animal data to one or more third parties or target individuals for consideration, the monitoring system being further configured to select one or more individuals to monitor with the at least one sensor and to identify which sensor or sensors are to be operated.

2. The system of claim 1 wherein the unmanned aerial vehicle analyzes the animal data before transmitting to the computing device, intermediary server, or a third-party.

3. The system of claim 1 wherein the unmanned aerial vehicle attaches metadata to the animal data before transmitting to a home station, intermediary server, or a third-party.

4. The system of claim 3 wherein the metadata includes characteristics of the animal data, origination of the animal data, or sensor data.

5. The system of claim 3 wherein one or more attributes related to (1) an individual from which the animal data originated, (2) the sensor, or (3) the animal data can be added to the metadata or associated with the animal data after the animal data is collected.

6. The system of claim 1 wherein if the unmanned aerial vehicle is not able to communicate with the at least one sensor, the unmanned aerial vehicle can be programmed to reconnect with the at least one sensor automatically after one or more of the following parameters change: time, location of the at least one sensor, location of one or more individuals, or location of one or more unmanned aerial vehicles.

7. The system of claim 1 wherein one or more communications between at least one sensor and a home station is handed off from a non-unmanned aerial vehicle transmission system to one or more unmanned aerial vehicles, and vice versa, within a network.

8. The system of claim 1 wherein a network including a home station, at least one sensor, and one or more unmanned aerial vehicles provide an ability to monitor one or more characteristics related to the at least one sensor, a sensor signal, and/or collected animal data.

9. The system of claim 1 wherein a home station is programmed to automatically select one or more unmanned aerial vehicles to connect with the at least one sensor based on one or more of following characteristics: unmanned aerial vehicle location, unmanned aerial vehicle payload, unmanned aerial vehicle bandwidth, individual location, sensor location, battery life, signal strength, environmental conditions, or signal quality.

10. The system of claim 9 wherein the home station or UAV (1) detects and monitors one or more characteristics related to signal quality and/or signal strength between the at least one sensor and one or more unmanned aerial vehicles across one or more data communication points, and (2) provides one or more commands to the sensor to pair with a secondary transmission source which may be another unmanned aerial vehicle or other non-unmanned aerial vehicle transmission system.

11. The system of claim 1 wherein one or more unmanned aerial vehicles can act within a single network, a plurality of networks, or independently of each other, with one or more home stations communicating with one or more unmanned aerial vehicles, and two or more unmanned aerial vehicles communicating with each other.

12. The system of claim 1 wherein one or more unmanned aerial vehicles is attached to another apparatus.

13. The system of claim 1 wherein an unmanned aerial vehicle is a home station or an intermediary server.

14. The system of claim 1 wherein one or more unmanned aerial vehicles have attached, affixed, or embedded at least one sensor that capture one or more data points and either (1) relay animal data to either a home station and/or a third-party or intermediary server, or (2) use at least a portion of captured animal data to transform captured sensor animal data into an insight or metric.

15. The system of claim 1 wherein the unmanned aerial vehicle is able to communicate with the at least one sensor from one or more individuals using one or more communication protocols.

16. The system of claim 1 wherein a home station monitors one or more unmanned aerial vehicles and/or the at least one sensor, with an event occurring that (1) alerts the home station, intermediary server, or third-party, and/or (2) prompts the home station to take at least one corrective action in furtherance of delivering an expected output to either the home station, intermediary server or third-party.

17. The system of claim 1 wherein a network consisting of a home station, at least one sensor and one or more unmanned aerial vehicles provides an ability to obfuscate any data being transmitted to/from sensors, home station or unmanned aerial vehicles.

18. The system of claim 1 wherein the animal data is human data.

19. The system of claim 1 wherein the unmanned aerial vehicle and/or a home station is operable to assign one or more classifications to the animal data, the one or more classifications including metric classifications, insight classifications, data properties, data timeliness classifications, or data context classifications.

20. The system of claim 1 wherein the at least one sensor is affixed to, or is in contact with, or is in electronic communication with a subject's body, eyeball, or skeletal system, embedded in at least one target individual, lodged in at least one target individual, ingested by an individual, or integrated as part of, affixed to, or embedded within, a fabric, textile, cloth, material, fixture, object, or apparatus that contacts or communication with at least one target individual either directly or via one or more intermediaries.

21. The system of claim 20 wherein the sensor is a biosensor that gathers physiological, biometric, chemical, biomechanical, location, environmental, genetic, genomic, or other biological data from one or more targeted individuals.

22. The system of claim 20 wherein the sensor gathers at least one of facial recognition data, eye tracking, biosignals, bioelectrical signals, blood flow, blood analysis, blood pressure, biological fluid, pulse, oxygenation, core body temperature, skin temperature, perspiration levels, location data, location coordinates, audio data, biomechanical movement, glucose levels, hydration levels, lactate levels, sodium levels, potassium levels, heart rate, genetic information, genomic data, skeletal data, muscle activity, breathing rate, position or accelerations in various directions, ambient temperature and humidity, barometric pressure, and elevation, or a combination thereof.

23. The system of claim 1 wherein the computing device executes a control application that executes one or more commands on the unmanned aerial vehicle, the commands initiating at least one of or any combination of (1) streaming of at least a portion of collected animal data in real time or near real time back to the control application, intermediary server, or third-party platform; (2) selecting one or more data streams to be sent back to the control application, intermediary server, or third-party system; (3) selecting a frequency upon which data is sent back to the control application, intermediary server, or third-party system; (4) transforming collected animal data on the unmanned aerial vehicle to a computed asset, with collected animal data being from the at least one sensor, and sending one or more computed assets to the control application, intermediary server, or third-party system; (5) aggregating one or more data streams on the unmanned aerial vehicle from at least one sensor to create one or more transformed data that can be sent back to the control application, intermediary server, or third-party system; (6) changing or adjusting settings within the at least one sensor; (7) instructing the at least one sensor to perform an action; (8) changing or adjusting a location of one or more unmanned aerial vehicles; or (9) storing sensor data.

24. The system of claim 1 wherein the unmanned aerial vehicle includes a data acquisition unit that communicates with the at least one sensor.

25. The system of claim 24 wherein the data acquisition unit includes a transceiver module that communicates with the sensor via a two-way communication link in which a user can activate and set one or more parameters for the at least one sensor and receive one or more data signals from the at least one sensor.

26. The system of claim 25 wherein the transceiver module is operable to communicate with a home station, third-party, and/or an intermediary server.

27. The system of claim 24 wherein the data acquisition unit includes a microprocessor operable to execute one or more data processing steps.

28. The system of claim 27 wherein the data acquisition unit includes a memory module and an input/output module in electrical communication with the microprocessor.

29. The system of claim 24 wherein the data acquisition unit includes a communication module.

30. The system of claim 1 wherein the consideration is a payment or a trade for something of value.

31. The system of claim 1 wherein the consideration is lion-monetary.

32. The system of claim 1 wherein the unmanned aerial vehicle detects a health or medical condition based upon collected animal data, which triggers either an alert or at least a portion of collected animal data being sent by the unmanned aerial vehicle to one or more home stations, intermediary servers or third-parties.

33. The system of claim 1 wherein the unmanned aerial vehicle is an aircraft that is piloted by remote control or autonomous onboard computers, without an onboard human presence.

34. The system of claim 1 wherein one or more unmanned aerial vehicles adjust their location or transceiver positioning based upon a location of at least one sensor or one or more individuals.

35. The system of claim 1 wherein the one or more unmanned aerial vehicles include a camera, optical trackers, weather trackers, or a combination thereof, to provide one or more videos or photographs, location tracking, facial recognition, wind, temperature, or humidity.

\* \* \* \* \*